United States Patent [19]

Varanasi et al.

[11] Patent Number: 5,514,799
[45] Date of Patent: May 7, 1996

[54] 1,1-VINYL SUBSTITUTED NONLINEAR OPTICAL MATERIALS

[75] Inventors: Pushkara R. Varanasi, Monmouth Junction; Kwan-Yue A. Jen, Old Bridge; King Y. Wong, Monmouth Junction; Robert M. Mininni, Stockton, all of N.J.

[73] Assignee: Enichem S.p.A., Italy

[21] Appl. No.: 101,368

[22] Filed: Aug. 2, 1993

[51] Int. Cl.$^6$ .................................................. C07D 239/02
[52] U.S. Cl. ..................... 544/300; 544/301; 544/225; 544/243; 544/141; 544/146; 548/106; 548/108; 548/524; 548/526; 548/577; 548/112; 549/32; 549/35; 549/39; 549/59; 549/74; 549/78; 252/501.1; 252/518; 252/519; 252/582
[58] Field of Search ...................... 549/59, 35, 39, 549/32, 74, 78, 59; 548/106, 108, 524, 526, 577, 112; 544/301, 300, 225, 243, 141, 146; 252/501.1, 518, 519, 582

[56] References Cited

U.S. PATENT DOCUMENTS

| | | |
|---|---|---|
| 4,892,681 | 1/1990 | Miyata et al. ......................... 252/582 |
| 4,894,186 | 1/1990 | Gordon et al. ........................ 252/582 |
| 4,894,263 | 1/1990 | Dubois et al. ........................ 428/1 |
| 4,933,112 | 6/1990 | DeMartino et al. .................. 252/587 |
| 4,935,292 | 6/1990 | Marks et al. ......................... 428/220 |
| 4,981,614 | 1/1991 | Miyazaki et al. .................... 252/587 |
| 5,156,774 | 10/1992 | Leising et al. ...................... 252/582 |

FOREIGN PATENT DOCUMENTS

| | | |
|---|---|---|
| 364313 | 4/1990 | European Pat. Off. . |
| WO91/03001 | 3/1991 | WIPO . |

OTHER PUBLICATIONS

Rossi, "Polyimides," *Engineered Materials Handbook, vol. 3: Adhesives and Sealants*, 151–62 (ASM International, Materials Park, Ohio 1991).

Nicoud et al., Ch. II–III of *Nonlinear Optical Properties of Organic Molecules and Crystals, vol. 1*, (Chemla and Ziss, Eds., Academic Press, Inc., New York 1987) 227–96.

Jen et al., U.S. Ser. No. 07/930,732, " Functionalized Heteroaromatics For NLO Applications", Filed Aug. 14, 1992.

Cernayova et al., *Collect Czech. Chem. Commun.*, 42(1), 347–52 (1977).

CA86:188704 Furan derivatives. LXXXI. Stereochemical . . . compounds. Cernayova et al., p. 510, 1977.

*Primary Examiner*—Joseph K. McKane
*Attorney, Agent, or Firm*—Lerner, David, Littenberg, Krumholz & Mentlik

[57] ABSTRACT

Nonlinear optical compounds having structures with delocalized resonance configurations corresponding to:

$$\begin{array}{c} D_1{\text{-}(R_1)}_n \\ D_2{\text{-}(R_2)}_m \end{array}\!\!\!\!>\!\!=\!\!<\!\!\!\!\begin{array}{c} A_1 \\ A_2 \end{array}$$

wherein $A_1$ and $A_2$ are independently selected from electron withdrawing moieties; $R_1$ and $R_2$ are independently selected from aromatic rings, heteroaromatic rings and fused ring systems consisting of two or three aromatic or heteroaromatic rings; n and m are integers from one to five, and $D_1$ and $D_2$ are independently selected from hydrogen, electron donating groups and polymer attachment groups, with the proviso that at least one of $D_1$ and $D_2$ is an electron donating group. Polymers blended with, cured with, or having pendant side chains of the disclosed nonlinear optical materials and exhibiting second order nonlinear optical properties are also disclosed.

35 Claims, No Drawings

# 1,1-VINYL SUBSTITUTED NONLINEAR OPTICAL MATERIALS

BACKGROUND OF THE INVENTION

1. Field of the Invention

The present invention relates to aromatic and heteroaromatic compounds with nonlinear optical (NLO) properties. In particular, the present invention relates to NLO compounds having improved chemical and thermal stability.

The compounds of the present invention are stable in processing solvents and at processing temperatures used in the production of electro-optic devices. When suitably oriented, the compounds are capable of highly efficient second harmonic generation and electro-optic modulation of an electromagnetic wave having a wavelength between 300 nm and 2,000 nm. The present invention further relates to polymer compositions of the disclosed compounds.

2. Description of the Prior Art

Highly efficient NLO materials capable of doubling or tripling the frequency of incident light are currently of great scientific and technological interest for use in optical telecommunications, signal processing and the construction of optical computers. Nonlinear optics is concerned with the interaction of electromagnetic fields in various media to produce new fields which may be altered in phase, frequency or amplitude. The NLO effect of a material upon an electromagnetic field is a function of the second and higher order terms of the following equation:

$$P = \alpha E + \beta E^2 \gamma E^3 + \ldots$$

P is the polarization of a material, E is the intensity of electric field, and the coefficients $\alpha$, $\beta$ and $\gamma$, etc. are indicative of the NLO susceptibility of the material. Such coefficients are constant for a given material, but vary from material to material. The second order coefficient, $\beta$, for a given material, is indicative of the second harmonic generation properties of the material, with second harmonic generation efficiencies increasing as the value of $\beta$ increases.

Candidate NLO materials should possess good physical properties, such as high optical transparency, low dielectric constant and high laser damage threshold. The materials should also possess the molecular nonlinearity required of NLO materials, in particular, high $\beta$ values, fast response times and nonlinear susceptibility over a broad range of wavelengths, particularly of wavelengths between about 300 nm and 2,000 nm.

Recent efforts in the development of NLO materials have focused upon non-centrosymmetric organic materials with large delocalized pi-electron systems, which exhibit great nonlinear susceptibilities and can be varied to optimize the desired physical and mechanical properties. This includes the single benzene ring derivative disclosed by U.S. Pat. No. 4,894,186 to Gordon and the compounds derived from two to four benzene rings separated by pi-electron conjugated carbon-carbon, carbon-nitrogen and nitrogen-nitrogen bridges disclosed by U.S. Pat. No. 4,892,681 to Myata et. al., U.S. Pat. No. 4,894,263 to Dubois et al., U.S. Pat. No. 4,933,112 to DeMartino et. al. and U.S. Pat. No. 4,935,292 to Marks et. al.

To induce charge asymmetry, and consequently second order nonlinear polarizability, an aromatic ring at one end of the NLO compound structure is substituted with an electron donating group, while on the other end of the NLO compound structure an aromatic ring is substituted with an electron accepting group. The dipole of the compound structure can then be aligned in accordance with the method described by U.S. Pat. No. 4,935,292, the disclosure of which is hereby incorporated herein by reference thereto.

Copending and commonly owned U.S. patent application Ser. No. 07/626,358 filed Dec. 12, 1990, discloses another group of NLO compounds containing from two to ten six-membered aromatic or five-membered heteroaromatic rings or fused ring systems linked together by the above-listed pi-electron conjugated bridges. At least one five-membered heteroaromatic ring is present by itself, or as part of a fused ring system, which heteroaromtic ring contains at least one heteroatom selected from O, N, S or Se. The five-membered heteroaromatic ring increases the extent of the electron delocalization associated with NLO activity and facilitates the enhancement of NLO activity as the number of aromatic rings increases. The disclosure of this patent application is hereby incorporated herein by reference thereto.

However, pi-electron conjugated bridges linking the aromatic or heteroaromatic rings of NLO compounds are a source of thermal and photochemical instability. This is addressed by copending and commonly owned U.S. patent application Ser. No. 07/930,732, filed Aug. 14, 1992, the disclosure of which is hereby incorporated herein by reference thereto. This application discloses NLO compounds derived from highly conjugated fused ring structures of two or three aromatic or heteroaromatic rings, at least one of which is a five-membered heteroaromatic ring. The pi-electron conjugated bridges are eliminated. This application also discloses NLO compounds derived from one to four non-fused five-membered heteroaromatic rings linked together without pi-conjugated bridges.

The stability of non-centrosymmetric organic materials with large delocalized pi-electron systems in processing solvents and host polymers at processing temperatures is an important parameter in their application in electro-optic devices. Because high-$T_g$ polyimide based electro-optic polymers are likely candidates to be used in the production of NLO devices, candidate NLO materials must survive the stringent processing conditions required to produce stable electro-optic polyimides. One of the commonly employed processing conditions requires the solubilization of candidate NLO materials in polyamic acid solutions using solvents such as N-methyl-pyrrolidone (NMP), dimethylacetamide (DMAC), dimethylformamide (DMF), and the like, and the curing of the resultant polymers at high temperatures (200°–300° C).

NLO compounds that are stable in solvents such as NMP, DMAC and DMF, both at room temperature and at boiling temperatures, are not well established in the literature. The general instability of NLO compounds in the solvents is attributable to the sensitivity of the electron accepting groups toward solvent decomposition products, typically open chain amine-type basic impurities induced by either light, oxygen or heat. Accordingly, a need exists for NLO compounds that are stable under polyimide curing and processing conditions.

SUMMARY OF THE INVENTION

NLO compounds have now been discovered that are chemically and thermally stable under polyimide processing conditions. The compounds contain a vinyl electron accepting group, the carbon-1 of which is di-substituted with electron-withdrawing moieties. The carbon-2 is di-substituted with pi-electron conjugated moieties having delocalized resonance configurations, wherein at least one of the moieties contains an electron donating group to induce charge asymmetry. The pi-conjugated moieties are limited to single aromatic or heteroaromatic rings or fused ring structures of two or three aromatic or heteroaromatic rings to ensure the thermal and photochemical stability of the NLO compound.

Therefore, in accordance with the present invention, there is provided a nonlinear optical compound corresponding to Formula I:

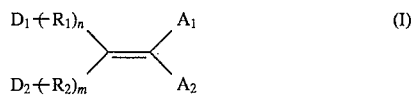

wherein $A_1$ and $A_2$ are independently selected from electron withdrawing moieties;

$R_1$ and $R_2$ are independently selected from aromatic rings, heteroaromatic rings and fused ring systems consisting of two or three aromatic or heteroaromatic rings;

n and m are integers from one to five;

$D_1$ and $D_2$ are independently selected from hydrogen, electron donating groups and polymer attachment groups, with the proviso that at least one of $D_1$ and $D_2$ is an electron donating group; and the compound formed by $A_1$, $A_2$, $D_1$, $D_2$, $R_1$ and $R_2$ possesses a delocalized resonance configuration.

Preferred NLO compounds of the present invention contain two electron donating groups, at least one of which may be substituted with a polymer attachment group. The electron withdrawing moieties may optionally be similarly substituted. $R_1$ and $R_2$ of preferred NLO compounds also contain at least one five-membered heteroaromatic ring, either as a single ring, or as a member of a fused ring system.

The NLO compounds of the present invention are uniquely stable under the curing conditions of polyamic acids in solvents such as NMP, and are stable in polyimides up to 300° C. By employing efficient electron donating groups and electron withdrawing moieties, and effective pi-conjugated units such as heteroaromatic rings (without pi-electron conjugated bridges) high molecular nonlinearity can be achieved without affecting the chemical and thermal properties. While not being bound by any particular theory, it is believed that the unique stability properties exhibited by the NLO compounds of the present invention can be attributed to the sterically locked, and thereby chemically inert, vinyl electron accepting group.

Another embodiment of the present invention provides a combination exhibiting second order NLO properties. This combination includes the NLO compounds of the present invention and a material chemically inert thereto. The NLO compounds of these combination preferably have an external field-induced molecular alignment.

In one aspect of this embodiment of the invention, the NLO compound is disposed as a layer or layers on a substrate of a material chemically inert thereto, such as glass, silica, silicon and polymeric materials. In another aspect of this embodiment of the invention, the NLO compound is in the form of a blend of a guest compound in a host matrix, with the NLO compound of the present invention serving as the guest compound and the material chemically inert thereto serving as the host matrix. The material that is chemically inert to the NLO compound is preferably a thermoplastic polymer selected from polyacrylates, polymethacrylates, polyurethanes, polyquinolines, epoxy polymers, polybenzoxazoles, polybenzothiazoles, polysulfones, polyacrylamides, polycarbonates, polyamides, polyesters, polystyrenes, polyimides, polyether ketones, polyether ether ketones, polyphenylene ethers and copolymers thereof.

In still yet another aspect of this embodiment of the present invention, pendant side chains of the NLO compounds of the present invention are covalently bonded to a polymer material chemically inert thereto. In accordance with a preferred aspect of this embodiment of the invention, $D_1$ or $D_2$ of the compound of Formula I is a polymer attachment group, preferably a functionalized alkyl moiety, that is covalently linked to a polymer. The polymer contains one or more monomeric subunits having a reactive group capable of being covalently attached to the polymer attachment group, whereby the compound of Formula I is covalently linked to the polymer at the reactive group of one of the subunits via the polymer attachment group.

Preferably, the polymer contains a plurality of the monomeric subunits having the reactive groups covalently substituted with an NLO compound via a polymer attachment group, so that the ratio of the monomeric subunits having reactive groups covalently linked to an NLO compound to monomeric subunits without an NLO compound covalently linked thereto is between 1:99 and about 50:50. The monomeric subunits having a reactive group capable of being covalently attached to a polymer attachment group and the monomeric subunits without an NLO compound covalently linked thereto are independently selected from polyacrylate, polyimide, polyquinoline, polybenzoxazole, polyurethane, polybenzothiazole, polysulfone, polyamide, polyacrylamide, polystyrene, polyvinyl halide, polyacrylonitrile, polyvinyl alcohol, polyvinyl acetate, polyester, polyethylene, polypropylene, polyisobutylene, polyisoprene, poly(acid anhydride) and polycarbonate monomeric subunits.

In yet another aspect of this embodiment of the present invention, the NLO guest compounds of the present invention are cross-linked within the host matrix. The NLO compound may function as the cross-linking agent that forms the host matrix, or the NLO compound may simply function as a guest compound within a cross-linked host matrix.

For the NLO compound of Formula I to function as a cross-linking agent, either $D_1$ or $D_2$ is a polymer attachment group, or either or both of $D_1$ and $D_2$ is an electron donating group substituted with a polymer attachment group. Either or both of $A_1$ and $A_2$ or $R_1$ or $R_2$ are also substituted with a polymer attachment group. Polymers capable of being cross-linked by an NLO compound in accordance with this aspect of the present invention include polyacrylates, polymethacrylates, polyurethanes, polyquinolines, epoxy polymers, polybenzoxazoles, polybenzothiazoles, polysulfones, polyacrylamides, polycarbonates, polyamides, polyesters, polystyrenes, polyimides, polyether ketones, polyether ether ketones, polyphenylene ethers and copolymers thereof.

Polymers that are capable of being independently cross-linked to form a host matrix for an NLO guest compound include epoxy polymers, polyimides, polyurethanes, polyamides, polyacrylates, and the like.

The NLO compounds of the present invention possess heretofore unattained chemical and thermal stability, without sacrificing second order nonlinearity. In addition to possessing good second order NLO susceptibilities and thermal and chemical stability, the compounds of the present invention are soluble in polymer matrices and spin-casting solvents, have high laser damage thresholds, are easily synthesized and have well-known and understood chemical properties.

DETAILED DESCRIPTION OF THE PREFERRED EMBODIMENT

The NLO compounds of the present invention, once suitably oriented, exhibit a high second order NLO susceptibility. Compounds suitable for use as second order NLO chromophore materials according to the present invention have the structure of Formula I in which $R_1$ and $R_2$ are single aromatic or heteroaromatic rings, or fused ring systems containing two or three aromatic or heteroaromatic rings. The variables n and m for $R_1$ and $R_2$, respectively, represent integers from one to five, inclusive, and are preferably one, two or three. $R_1$ and $R_2$ may be the same or different and do not contain aromatic or heteroaromatic rings separated by pi-conjugated bridges.

Within the present specification "aromatic" rings are defined as aromatic carbocyclic rings such as benzene rings. "Heteroaromatic" rings refer to aromatic heterocyclic rings, thereby excluding aromatic carbocyclic rings such as benzene and nonaromatic heterocyclic rings such as pyrrolidine.

Preferably, at least one of $R_1$ or $R_2$ is a single five-membered heteroaromatic ring or a two- or three-ring fused ring system containing at least one five-membered heteroaromatic ring, which five-membered heteroaromatic ring has one heteroatom selected from O, N, S, Se and Te. The heteroaromtic ring may optionally include up to three additional N atoms. Preferably, the five-membered heteroaromatic rings possess a structure corresponding to Formula II:

(II)

in which Y is C or N and X is selected from O, N, S, Se and Te.

More preferably, both $R_1$ and $R_2$ are either single five-membered heteroaromtic rings or fused ring systems containing at least one five-membered heteroaromatic ring. Even more preferably, both $R_1$ and $R_2$ are two-or three-ringed fused ring systems containing at least one five-membered heteroaromatic ring. Still even more preferred are such fused ring systems containing two or three five-membered heteroaromatic rings. When two or more heteroaromatic rings are present in a fused ring system, the rings may have the same or different heteroatoms.

The fused ring systems, when present, should not be so large as to hinder the solubility of the NLO compounds in polymer matrices or spin-casting solvents. Likewise, the values of n and m should not be so high as to interfere with solubility. The point at which the number of single or fused rings, or fused ring system size, interferes with solubility is easily identified by those of ordinary skill in the art.

The configuration of multiple heteroaromatic rings within a fused ring system is not critical, and may be an all "up" configuration or an alternating "up" and "down" configuration, as depicted in the above-cited U.S. patent application Ser. No. 930,732, the disclosure of which is hereby incorporated herein by reference thereto.

The fused ring systems of the present invention are not limited to structures containing only five-membered heteroaromatic rings. Two-ring fused ring systems suitable for use with the present invention may also contain a benzene or pyridine ring. Three-ring fused ring systems suitable for use with the present invention may contain up to two benzene or pyridine rings, or a benzene and a pyridine ring, in addition to the five-membered heteroaromatic ring. Thus, the fused ring systems of the present invention include such structures depicted in the above-mentioned U.S. patent application Ser. No. 930,732. When a two- or three-ring system includes pyridine, the pyridine should not be quaternized. Such ionic species cause severe current leakage during the dipole-alignment electric field poling process.

From the foregoing description, the aromatic and fused ring systems represented by $R_1$ and $R_2$ that are suitable for use with the present invention can be easily identified by those of ordinary skill in the art. Suitable rings and ring systems include, but are not limited to, pyrrole, furan, thiophene, imidazole, oxazole, thiazole, triazole, tetrazole, pyrazole, pyrimidine, purine, quinolines, carbazole, benzene, naphthalene, furazan, pyrazine, indole, isoindole, indazole, phenothiazine, benzotriazole, anthracene, phenanthrene, azophenanthrenes, quinazolines, pteridine, and the like.

To induce charge asymmetry, the NLO compounds of the present invention contain at least one electron donating group and an electron accepting group containing two electron withdrawing moieties. The portion of the compound of Formula I that functions as an electron accepting group is depicted below as Formula IA:

(IA)

$A_1$ and $A_2$ represent electron withdrawing moieties. The compound of Formula I also contains at least one electron donating group, represented by $D_1$, $D_2$, or both.

The positions at which the electron withdrawing moieties are located are essentially fixed. This contributes to the thermal and chemical stability of the NLO compounds of the present invention. Because they are ring-substituted, the position of the electron donating group or groups is more variable. However, the electron donating group or groups should be substituted so as to form a delocalized resonance configuration. Positions for substituting electron donating groups to form delocalized resonance configurations can be readily determined by those of ordinary skill in the art.

When $R_1$ or $R_2$ represent fused ring systems containing five-membered heterocyclic rings, the electron donating and electron accepting groups are preferably substituted on the five-membered heterocyclic ring members of the fused ring systems, although this is not essential. When substituted on five-membered heterocyclic rings, the electron donating group or electron accepting group is preferably substituted alpha to a heteroatom. Regardless of whether the fused ring system contains a five-membered heteroaromatic ring, the electron donating and accepting groups are preferably substituted to ring members of different rings so as to form a delocalized resonance configuration. Examples of typical delocalized resonance configurations are depicted in the above-cited U.S. patent application Ser. No. 930,732.

The electron withdrawing moieties that form electron accepting group so as to induce charge asymmetry to the structure of Formula I are essentially conventional to the art of NLO active organic materials. Guidance for the selection of electron withdrawing moieties can be found in Nicoud et. al., Ch. II-3 of *Nonlinear Optical Properties of Organic Molecules and Crystals*, Vol. 1 (Chemla and Zyss, Eds., Academic Press, Inc., New York 1987), p. 233. Essentially any functional group capable of withdrawing electrons from the pi-electron system of an aromatic or heteroaromatic ring or a fused ring system is suitable for use as the electron withdrawing moieties, $A_1$ and $A_2$.

Examples of suitable electron withdrawing moieties known in the art from which $A_1$ and $A_2$ may be independently selected include —$NO_2$, —CN, —CHO, —$COR_5$, —$COOR_5$, —$PO(OR_5)_2$, —$SO_2R_5$, —$SO_3R_5$ and —$PO(R_5)_2$, wherein $R_5$ is an alkyl group containing up to 15 carbon atoms, and preferably is a methyl group. $A_1$ and $A_2$ may also together form a ring structure. Preferred ring structures include N,N-dialkylbarbituric acids, N,N-dialkylthiobarbituric acids, rhodamines, hydrantoins, oxazolines, and a ring system corresponding to the electron accepting group of Formula IA and having the structure of Formula III:

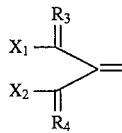
(III)

wherein $X_1$ and $X_2$ form a saturated or unsaturated five- to eight-member cyclic ring or two-ring system having five- to eight-membered rings, and $R_3$ and $R_4$ are independently selected from O, S and $-Cl_1I_2$, wherein $I_1$ and $I_2$ are independently selected from $-CN$, $-NO_2$, $-COR_5$, $-COOR_5$, $-SO_2R_5$, $-PO(R_5)_2$ and $-PO(OR_5)_2$. Again, $R_5$ is an alkyl group containing up to 15 carbon atoms, and preferably is a methyl group. Examples of ring structures defined by the structure of Formula III include 3-dicyanovinylindane-1-sulfone, 1,3-bissulfonylindane, indane-1,3-dione, 3-dicyanovinylindane-1-one and 1,3-bisdicyanovinyl indane.

Strong electron withdrawing moieties are preferred, examples of which include $-CN$ and $-NO_2$. Strong electron withdrawing ring structures formed by $A_1$ and $A_2$ are also preferred, examples of which include the N,N-dialkylbarbituric acids, N,N-dialkylthiobarbituric acids, rhodamines, hydrantoins, oxazolines, and the ring structure of Formula III, which significantly increase the second order NLO properties of the compounds of the invention.

Electron donating groups that are used to induce charge asymmetry to the structure of Formula I are also essentially conventional to the art of NLO active organic materials. Guidance for the selection of electron donating groups can also be found in Nicoud et al. Essentially any functional group capable of releasing electrons into the pi-electron system of an aromatic or heteroaromatic ring or fused ring system is suitable for use as the electron donating group or groups, $D_1$ and $D_2$.

Examples of suitable electron donating groups known in the art include $-NR_6R_7$, $-OR_8$, $-SR_8$, $-TeR_8$, $-SeR_8$, $-CH=NR_9$, $-CH=N-NR_6R_7$, and $-CH=C[N(R_6R_7)]_2$, wherein $R_6$ and $R_7$ are independently selected from hydrogen, alkyl groups containing up to 12 carbon atoms and alkyl groups containing up to 12 carbon atoms having reactive functional groups selected from hydroxyl, ethylene, acetylene, amine, thiol, sulfonic acid, carboxylic acid, or $R_6$ and $R_7$ together form a cyclic group containing up to 8 carbon atoms, including groups such as pyrrolidine, piperidine, piperazine and morpholine. $R_8$ is an alkyl group containing up to six carbon atoms and $R_9$ is hydrogen or an alkyl group containing up to 10 carbon atoms. Preferably, $R_6$ and $R_7$ are independently selected from methyl, ethyl, hexyl, cyclopentyl, cyclohexyl, pyrrolidine, piperadine, piperazine and morpholine, $R_8$ is preferably a methyl group and $R_9$ is preferably either hydrogen or a methyl group.

Another example of suitable electron donating groups are the functional groups:

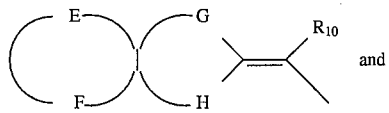

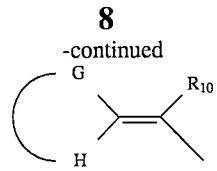

wherein E, F, G and H are members of a saturated or unsaturated five- to eight-membered cyclic ring or two-ring system having five- to eight-membered rings that are electron donating in nature. E, F, G and H are heteroatoms independently selected from $-CH-$, $-CH_2-$, O, N, S, Se, Te and $-NR-$. R and $R_{10}$ are independently selected from hydrogen, alkyl moieties containing up to 18 carbon atoms and functionalized alkyl moieties containing up to 18 carbon atoms, wherein the functionalized alkyl moieties are selected from alkoxy, aminoalkyl, alkylhalide, hydroxyalkyl, alkylsulfide, alkylisocyanate, alkylisothiocyanate, alkylthiol, alkylazide, alkylcarboxylic, alkylsulfonic, alkylalkene and alkylalkyne moieties.

Examples of suitable one- or two-ring electron donating groups include dithiane and dithiolium groups such as 1,3-dithiolium, 2-benzo-1,3-dithiolium and 2-ethylenedithio-1,3-dithiolium, and the like. Whether or not a ring is electron donating in nature to meet the definition of membership in the group is understood by those of ordinary skill in the art.

Strong electron donating groups are preferred, which significantly increase the second order NLO properties of the compounds of the invention. Examples of strong electron donating groups are $-N(CH_3)_2$, pyrrolidine, dithiane, piperidine, piperazine, morpholine and dithioliums such as 1,3-dithiolium, 2-benzo-1,3-di-thiolium and 2-ethylenedithio-1,3-dithiolium. The most preferred strong electron donating group is 2-ethylene-dithio-1,3-dithiolium.

The aromatic or heteroaromatic rings or fused ring systems of the NLO compounds of the present invention may optionally be further substituted. Any number of functional groups can be substituted on the aromatic or heteroaromatic ring or rings, provided that the groups are not so large or so numerous to cause undesirable steric hindrance effects, the occurrence of which will be clear to those of ordinary skill in the art.

The NLO compounds of the present invention may optionally include up to two polymer attachment groups. These groups are functionalized substituents that serve as means for attaching the NLO compound to a polymer chain. The presence of one polymer attachment group allows the covalent attachment of the NLO compounds of the present invention as side chains to the monomeric subunits with polymers. When two polymer attachment groups are present, the NLO compounds are capable of cross-linking polymer matrix polymers.

Thus, $D_1$ or $D_2$ can be a functionalized moiety capable of covalently linking the NLO compound to a monomeric subunit of a polymer by conventional addition or condensation reactions. Alternatively, either or both of $D_1$ or $D_2$ can be an electron donating group functionalized with an appropriate substituent for covalent attachment of the NLO compound to a polymer subunit. The electron withdrawing moieties and the aromatic or heteroaromatic rings or fused ring systems of the present invention can be functionalized with appropriate substituents for covalent attachment of NLO compounds to polymer subunits. Substituent groups suitable for the covalent attachment of NLO compounds to polymer subunits are well-known to those of ordinary skill in the art. Examples of polymer attachment groups include functionalized alkyl moieties containing up to 18 carbon atoms, wherein the functionalized alkyl moieties are selected from alkoxy, aminoalkyl, alkylhalide, hydroxyalkyl, alkylsulfide, alkylisocyanate, alkylisothiocyanate, alkylthiol, alkylazide, alkylcarboxylic, alkylsulfonic, alkylalkene and alkylalkyne moieties.

Preferred polymer attachment groups will also increase the solubility of the materials both in polymer matrices and in spin-casting solvents. Ordinarily, the solubility would decrease as the number of rings or fused ring systems in the non-centrosymmetric organic moiety increases. Substituents that will increase the solubility of the non-centrosymmetric organic moieties are well-known to those of ordinary skill in the art. Preferred substituents include alkyl moieties containing between 3 and 12 carbon atoms and functionalized alkyl moieties containing between 3 and 12 carbon atoms, wherein the functionalized alkyl moieties are selected from alkoxy, aminoalkyl, alkylhalide, hydroxyalkyl, alkylsulfide, alkylthiol, alkylazide, alkylcarboxylic, alkylsulfonic, alkylalkene, alkylisocyanate, alkylisothiocyanate and alkylalkyne moieties.

The fused ring systems upon which the NLO compounds of the present invention may be based are prepared by well-known methods widely reported in the prior art. The preparation of many of these moieties is disclosed in the above-cited U.S. patent application Ser. Nos. 626,358 and 930,732. Some of the rings and fused ring systems are commercially available. The electron accepting group containing the electron withdrawing moieties and the electron donating groups can be substituted to the aromatic or heteroaromatic rings or fused ring systems using conventional methods.

A general procedure for the preparation of the NLO compound of the present invention, in which an electron donating group substituted aromatic or heteroaromatic ring or fused ring system is reacted with a cyanoethylene compound is illustrated by the following reaction scheme:

Scheme I

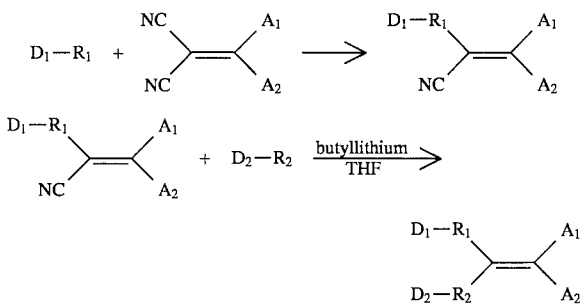

$D_1$, $D_2$, $R_1$, $R_2$, $A_1$ and $A_2$, and the preferred species thereof, are the same as described above with respect to Formula I. Two alternative reaction schemes are shown below:

Scheme II

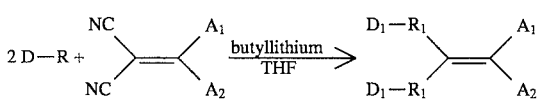

Scheme III

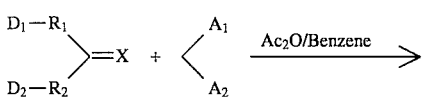

-continued
Scheme III

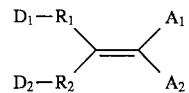

Again, $D_1$, $D_2$, $R_1$, $R_2$, $A_1$ and $A_2$, and the preferred species thereof are the same as described above with respect to Formula I. X is NH or S.

The NLO compounds of the present invention can be formed into a nonlinear optical material by combining the NLO compounds with a medium that is chemically inert to the compounds. For example, the NLO compounds can be layered on a substrate such as glass, silica or polymeric materials, as described in U.S. Pat. No. 4,894,186 to Gordon, the disclosure of which is hereby incorporated herein by reference thereto.

In another embodiment, a nonlinear optical medium can be formed by blending the NLO compounds of the present invention with a host thermoplastic polymer. Suitable host thermoplastic polymers include polyacrylates, polymethacrylates, polyurethanes, polyquinolines, epoxy polymers, polybenzoxazoles, polybenzothiazoles, polysulfones, polyacrylamides, polycarbonates, polyamides, polyesters, polystyrenes, polyimides, polyether ketones, polyether ether ketones, polyphenylene ethers and copolymers thereof. This combination is also described in U.S. Pat. No. 4,894,186, the disclosure of which is also hereby incorporated herein by reference thereto.

The NLO compounds of the present invention can also be covalently attached as side chains to the monomeric subunits of polymers. Polymers should be chosen for use with the present invention having monomeric subunits that have reactive functional groups for attachment of side chains. The polymer should have excellent optical transparency, good film-forming characteristics, a low dielectric constant and a relatively high $T_g$ for stable dipole orientation of the side chains. Other properties will come into consideration, depending upon the particular end-use requirements of the material; however, these properties are well-understood by those of ordinary skill in the art.

One class of polymers suitable for use with the present invention are polymers and copolymers, the monomeric subunits of which are independently selected from polyacrylate, polyimide, polyquinoline, polybenzoxazole, polyurethane, polybenzothiazole, polysulfone, polyamide, polyacrylamide, polystyrene, polyvinyl halide, polyacrylonitrile, polyvinyl alcohol, polyvinyl acetate, polyester, polyethylene, polypropylene, polyisobutylene, polyisoprene, poly(acid anhydride) and polycarbonate monomeric subunits.

The polyacrylates suitable for use with the present invention include alkyl branched polyacrylates such as polymethacrylates. Likewise, the polyacrylamides suitable for use with the present invention include alkyl branched polyacrylamides such as polymethacrylamide, and the polyacrylonitriles include alkyl-branched polyacrylonitriles such as polymethacrylonitrile.

Those of ordinary skill in the art are capable of identifying the functional groups of the polyacrylates, polyamides, polyacrylamides, polyvinyl-halides, polyacrylonitriles, polyvinyl alcohols, polyvinyl acetates, polyesters, polyphenylene ethers, polyether imides, polyether ketones, polyether ether ketones, polyacid anhydrides and polycarbonates to which the NLO compound of the present invention can be attached by conventional addition and condensation reactions.

Although the monomeric subunits of polyimides, polystyrene, polyethylene, polypropylene, polyisobutylene and polyisoprene do not have such functional groups, such monomeric subunits can first be functionalized to form a reactive group for the attachment of the NLO compound. See, for example, the chloromethylation of polystyrene and the subsequent conversion to the more reactive iodomethyl derivative set forth in U.S. Pat. No. 4,935,292 to Marks, the disclosure of which is herein incorporated by reference thereto.

Alternatively, a functionalized derivative of these polymers can be used as a starting material, such as the poly(p-hydroxystyrene), the use of which is also disclosed by U.S. Pat. No. 4,935,292. As another alternative, rather than covalently bond the materials, the polymers can be polymerized in the presence of the NLO compounds of the present invention so that a host polymer matrix is formed within which the NLO compound is present as a guest molecule.

The NLO compounds of the present invention are attached to the monomeric subunits by the polymer attachment groups discussed above. The polymer attachment group is covalently linked to the polymer at a reactive functional group of one of the monomeric subunits suitable for attachment of the NLO compound. Thus, the NLO compounds are covalently linked to a polymer at the reactive groups of the monomeric subunits via polymer attachment groups on the NLO compounds.

The NLO compounds of the present invention can be attached as polymer side chains by using a single polymer attachment group to covalently bond the NLO compounds to monomeric subunits of the polymer. The NLO compounds can also be attached between two or more monomeric subunits using multiple polymer attachment groups, thereby cross-linking polymer chains. For either embodiment, $A_1$, $A_2$, $D_1$, $D_2$, $R_1$, $R_2$ and the preferred species thereof are the same as described above with respect to Formula I.

Polymers in accordance with this aspect of the present invention will not be completely substituted with NLO groups. The present invention includes polymers having ratios of NLO substituted monomeric subunits to unsubstituted monomeric subunits between about 1:99 and about 50:50. Substitution ratios between about 5:95 and about 40:60 are preferred. Substitution ratios less than about 30:70 are more preferred in order that the polymer remains soluble in solvents utilized in the preparation of NLO materials. The most preferred substitution ratio is about 25:75.

In preferred NLO polymers, the monomeric subunits are independently selected from monomers of ethylene, acrylates, alkyl-branched acrylates, polyimides, acrylamides, alkyl-branched acrylamides, styrenes, alpha-alkyl styrenes, vinyl acetate, ether ketones and ether ether ketones. When one of the monomeric subunits is a styrene monomer, the aromatic ring may be further substituted by one or more hydroxyl or alkyl groups, provided that the groups are not so large or so numerous to cause undesirable steric hindrance effects, the occurrence of which will be clear to those or ordinary skill in the art. In the most preferred NLO polymers, the monomeric subunits are independently selected from monomers of acrylates, methacrylates, polyimides, ether ketones and ether ether ketones.

The polymerization of the polymeric NLO materials of the present invention is essentially conventional and is readily understood by those of ordinary skill in the art. Depending upon the material in question, in some cases, it is preferably first to polymerize the polymer and then attach the side chains to the reactive groups of the monomeric subunits. In other cases, it is preferable to synthesize a monomer having an NLO side chain covalently attached thereto to be copolymerized with a monomer having no side chain. The NLO polymers are then recovered and purified by conventional means known to those of ordinary skill in the art.

Polymers that are particularly preferred for the production of nonlinear optical devices are the polyimides. Polyimides are formed by the reaction of an aromatic diamine with an aromatic dianhydride to form a polyamic acid, which then undergoes a ring-closing reaction to form the polyimide structure. The cyclization to the polyimide is accomplished by a thermally induced intramolecular condensation. This is performed at elevated temperatures around 200°–300° C. in solvents like NMP, DMAC and DMF, for which the NLO compounds of the present invention are particularly well suited because of their thermal and chemical stability under these conditions.

The NLO compounds of the present invention may simply be dissolved in polyamic acid solutions, which are then cured to form a polyimide matrix containing the NLO compounds. The polyimide may be thermoplastic or it may be thermosetting. The NLO compounds of the present invention may also be covalently attached to the polyimide by formation of a polyamic acid with NLO side chain-substituted aromatic rings that is subsequently cured to form the polyimide. Polyamic acids having NLO side chain substituted aromatic rings are obtained by forming the polyamic acid from aromatic diamines or aromatic dianhydrides, or both, that are ring-substituted with side chains of the NLO compounds of the present invention. The preparation of such ring-substituted diamines and dianhydrides is essentially conventional and well-understood by those of ordinary skill in the art.

The NLO compounds of the present invention can be linked to two aromatic diamines or two aromatic dianhydrides, or to an aromatic diamine and an aromatic dianhydride so as to form a cross-linked polyamic acid. The cross-linked polyamic acid is then cured to form a polyimide cross-linked by the NLO compounds of the present invention.

The preferred NLO polymers of the present invention typically have weight-average molecular weights between about 5,000 and about 300,000 daltons measured by GPC or light scattering. Films of the polyimides and other polymers may be formed by spin-coating, after which the films may be repetitively annealed prior to poling at an elevated temperature at the $T_g$ of the material. Following annealing, the dipoles of the side chains may be aligned by application of an intense electric field, (0.2–3.0 MV cm$^{-1}$) at temperatures near the $T_g$.

Because of the high $T_g$'s of polyimides, the annealing and dipole aligning steps for these polymers is typically performed at temperatures greater than 200° C. The NLO compounds of the present invention possess the chemical and thermal stability required for these conditions. Such conditions are also encountered when forming electro-optic devices from the polyimide-linked NLO compounds of the present invention. The foregoing sequence of spin-coating, annealing and poling is essentially conventional and disclosed in U.S. Pat. No. 4,935,292, the disclosure of which is hereby incorporated herein by reference thereto.

It is disclosed in U.S. Pat. No. 4,935,292 and SPIE Proceeding No. 1147, 74–83 (1989) that for non-cross-linked polymers, further stabilization of the NLO side chain alignment can be achieved by radiation-induced or chemical-induced cross-linking of the polymer matrix. This process is also essentially conventional, and the disclosure of which in U.S. Pat. No. 4,935,292 is also hereby incorporated herein by reference thereto.

The electro-optic coefficient of an NLO-active poled polymer film is proportional to the product of the molecular second order nonlinear optical susceptibility coefficient, $\beta$, and the molecular ground state electric dipole moment, $\mu$. The molecular $\beta$ is dependent upon the frequency at which the measurement is performed because of the resonance effect near the absorption peak. A method to compare molecules with different absorption properties by extrapolation of the $\beta$ value measured at a specific frequency to zero frequency using a two-level model is disclosed by Singer, J. Opt. Soc. Am., B6, 1339–50 (1989). The $\beta$ value of the extrapolated zero frequency is defined as $\beta_O$. The NLO active molecules of the present invention can exhibit values of the $\beta_O\mu$ product as hjigh as about 3,000 in units of $10^{-48}$esu measured at a wavelength of 1907 nm.

Thus, it can be appreciated that the present invention provides NLO compounds combining second order nonlinear optical properties with the physical, mechanical and optical properties required of an optical material, together with thermal and chemical stability. The following examples further illustrate the present invention, and are not to be construed as limiting the scope thereof. Unless otherwise indicated, materials were obtained from Aldrich Chemical Supply. All parts and percentages are by weight unless expressly indicated to be otherwise and all temperatures are in degrees Celsius.

EXAMPLES

EXAMPLE 1 - Preparation Of Bis-1,1-(2-(N-Pyrrolidino)-5-Thienyl)-2,2-Dicyanoethylene

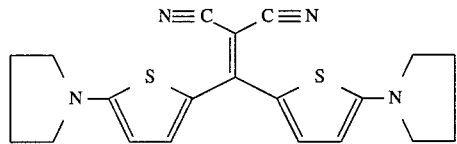

A solution of n-butyllithium (n-BuLi) in tetrahydrofuran (THF) (2.5 M, 4.0 mL, 10 mmol) was slowly added to a solution of 2-(N-pyrrolidino) thiophene (1.53 g, 10 mmol) in 100 mL THF at −78° C. The resulting mixture was maintained at −78° C. for one hour. A solution of tetracyanoethylene (0.64 g, 5 mmol) in 20 mL THF was then added dropwise to the reaction mixture. The mixture was allowed to warm to room temperature, and maintained at this temperature with stirring for two hours.

The reaction mixture was quenched with 100 mL water, and the resulting dark red colored aqueous solution was extracted with dichloromethane (4×200 mL). The combined extracts were dried (Na$_2$SO$_4$), concentrated under reduced pressure and eluted with dichloromethane on a silica column. This yielded the dark colored bis-1,1-(2-(N-pyrrolidino)-5-thienyl)- 2,2-dicyanoethylene 1 (1.14 g, 60% yield), the structure of which was confirmed by proton NMR spectroscopy. The product also showed characteristic UV spectra.

EXAMPLE 2 -Preparation Of 2-Hexanoylthiophene (2)

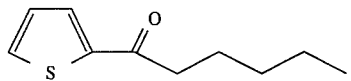

Thiophene (0.9 g, 10.7 mmol) and hexanoyl chloride (1.52 g, 11.3 mmol), both of which were obtained from Aldrich and used without further purification, were dissolved in benzene (20 mL) and cooled to 0° C. under argon. Stannic Chloride (10.7 mL, 10.7 mmol, 1 M solution in dichloromethane) was added dropwise and the resulting solution was stirred overnight. (Upon addition of the Stannic Chloride, the color changed from colorless to red.) After stirring overnight, 20 mL of a 50:50 mixture of concentrated hydrochloric acid and water was added. The resulting mixture was stirred for two hours whereupon the color became golden yellow. The organic layer was separated, washed with sodium bicarbonate solution, dried (Na$_2$SO$_4$) and concentrated to yield 2-hexanoylthiophene 2 (1.83 g, 94% yield). The compound was further purified by column chromatography using hexane/dichloromethane as the elutant.

EXAMPLE 3 -Preparation Of 2-Hexyl-Thienyl-6-Ylidene-(2'-(1',3'-Benzodithiole))(3)

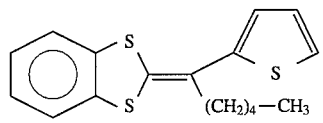

This compound was prepared by adding potassium t-butoxide (1.12 g, 10.0 mmol) to a −78° C. stirred solution of the 2-hexanoylthiophene 2 of Example 2 (1.82 g, 10.0 mmol) and 2-diethoxyphosphoryl-1,3benzodithiole (2.9 g, 10.0 mmol) in dried, freshly distilled, THF (50 mL) under an argon atmosphere. The 2-diethoxyphosphoryl-1,3-benzodithiole was prepared as described in *J. Org. Chem.*, 39, 2457 (1974). The resulting solution was stirred and slowly warmed to room temperature overnight under an argon atmosphere.

The mixture was concentrated in vacuo, and the residue was dissolved in dichloromethane, washed with water (3×200 mL), dried (Na$_2$SO$_4$), and concentrated onto approximately 5.0 g silica. This silica was added to a medium pressure column packed with silica. The column was eluted with a 3:1 ratio solution of hexane to dichloromethane with a gradient to 1:1 to yield the substituted thiophene 3 (2.86 g, 90% yield).

EXAMPLE 4 -Preparation Of 4-(N-Pyrrolidino) Tricyanovinylbenzene

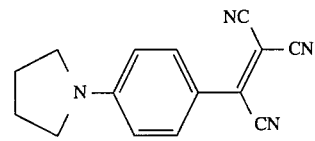

4-(pyrrolidino) tricyanovinylbenzene was prepared by mixing 1-phenylpyrrolidine (1.0 g, 6.8 mmol) with tetracyanoethylene (0.9 g, 7 mmol) in 10 mL dimethylformamide at 0° C. The reaction mixture was stirred at room temperature for three hours and at 40° C. for another ten hours. The reaction mixture was quenched with 25 mL water and the dark red colored aqueous solution was extracted with 150 mL methylene chloride and washed several times with water (150 mL). The organic layer was then separated, dried over Na$_2$SO$_4$ and evaporated. The crude products were purified through a silica gel column. The column was eluted with a 1:1 ratio solution of methylene chloride and hexane to yield 1.7 g of the pure product 4 (90% yield).

EXAMPLE 5

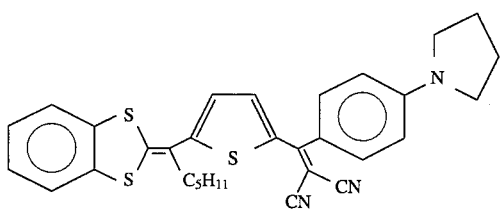

A dicyanovinyl compound of the present invention was prepared by adding n-butyllithium (2.5 M, 4 mL, 10 mmol) to a stirred solution of the compound 3 of Example 3 (3.18 g, 10 mmol) in 150 mL of dry THF at −78° C. under an argon atmosphere. The reaction mixture was stirred at −30° C. for one hour. The mixture was then added dropwise to a stirred solution containing the tricyano compound 4 of Example 4 (2.48 g, 10 mmol) in 25 mL of THF at −78° C. The resulting mixture was warmed to room temperature, stirred for five hours, then quenched with 10 mL water, evaporated, diluted with 300 mL dichloromethane and washed twice with water (150 mL). The organic layer was separated, dried over $Na_2SO_4$ and evaporated. The crude products were purified through a silica gel column. The column was eluted with a 10:90 ratio solution of methylene chloride and hexane to get 4.0 g of the pure product 5 (74% yield).

EXAMPLE 6

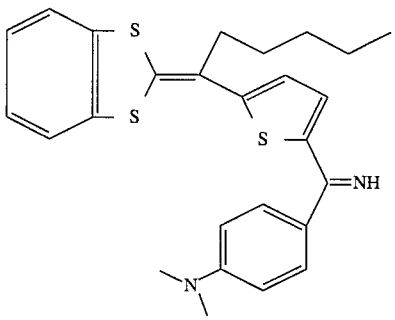

The substituted imine 6 was prepared by adding n-butyllithium (2.5 M, 3.8 mL, 9.5 mmol) to a stirred solution of the compound 3 of Example 3 (3.0 g, 9.25 mmol) in 100 mL of dry THF at −78° C. The resulting mixture was maintained at −30° C. for two hours. To this, 4-(dimethylamino) benzonitrile (1.35 g, 9.25 mmol) was added and the solution was slowly warmed to room temperature over a three hour period. The reaction was then quenched with 100 mL of water and the THF was removed under reduced pressure. The aqueous solution was extracted with methylene chloride, and the organic layer was separated, dried over $Na_2SO_4$ and evaporated. The crude products were purified through a silica gel column eluted with a 3:1 ratio solution of chloroform and ethyl acetate and yielded 3.5 g of the pure product 6 (75% yield).

EXAMPLE 7

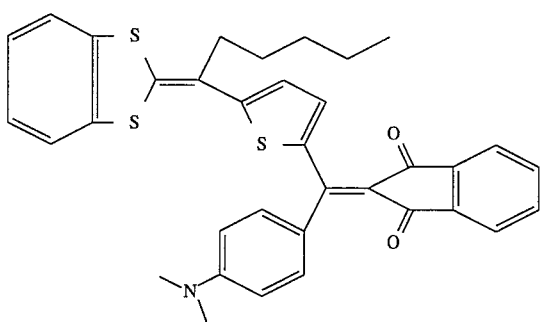

An indane-1,3-dione derivative 7 was prepared by mixing the substituted imine 6 of Example 6 (1.0 g, 2.12 mmol) with indane-1,3 dione (0.31 g, 2.12 mmol) in 20 mL benzene at room temperature. The reaction mixture was stirred at 50° C. for three hours and the benzene was removed at reduced pressure. The crude product was purified through a silica gel column eluted with a 1:1 ratio solution of methylene chloride and hexane to yield 1.0 g of the compound 7 (80% yield).

EXAMPLE 8

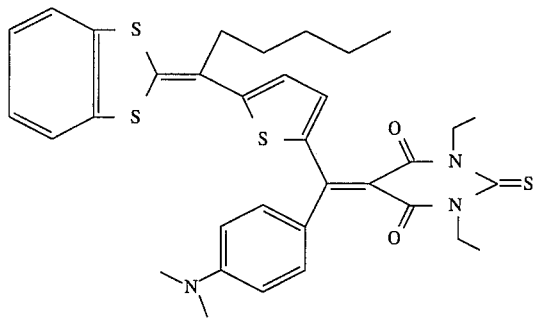

A 1,3-diethyl-2-thiobarbituric acid derivative 8 was prepared by mixing the substituted imine 6 of Example 6 (1.0 g, 2.12 mmol) with 1,3-diethyl-2-thiobarbituric acid (0.42 g, 2.12 mmol) in 15 mL acetic anhydride at room temperature. The reaction mixture was stirred at 40° C. for five hours and then quenched with 100 mL water. The resulting aqueous solution was extracted with methylene chloride, and the organic layer was separated, washed several times with water, dried over $Na_2SO_4$ and evaporated. The crude products were purified through a silica gel column eluted with a 9:1 ratio solution of methylene chloride and ethyl acetate to yield 0.97 g of the pure product 8 (70% yield).

EXAMPLE 9

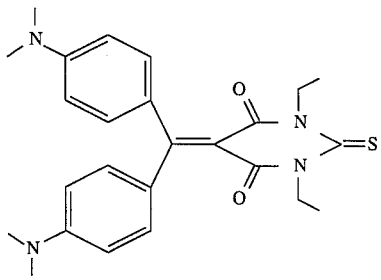

Compound 9 was prepared by mixing 4,4'-bis(dimethylamino) thiobenzophenone (2.84 g, 10 mmol) with 1,3-diethyl-2-thiobarbituric acid (2.0 g, 10 mmol) in 50 mL acetic anhydride. The reaction mixture was stirred at 60° C. for ten hours, cooled, and the reaction was then quenched with 250 mL water. The aqueous solution was extracted with methylene chloride and the organic layer was washed several times with water. The organic layer was then separated, dried over $Na_2SO_4$ and evaporated. The crude products were purified through a silica gel column eluted with a 9:1 ratio solution of methylene chloride and ethyl acetate to get 2.47 g of the pure product 9 (55% yield).

EXAMPLE 10

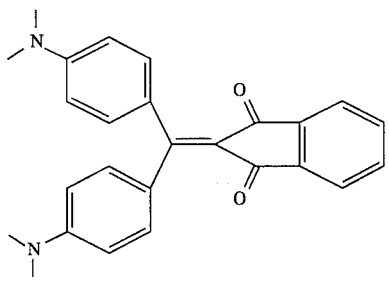

10

Compound 10 was prepared by mixing 4,4'-bis (dimethylamino) thiobenzophenone (2.84 g, 10 mmol) with indane-1,3-dione (1.46 g, 10 mmol) in 30 mL acetic anhydride. The reaction mixture was stirred at 50° C. for ten hours, and the reaction was then quenched with water. The aqueous solution was extracted with methylene chloride and the organic layer was washed several times with water. The organic layer was then separated, dried over $Na_2SO_4$ and evaporated. The crude products were purified through a silica gel column eluted with a 1:1 ratio solution of methylene chloride and hexane to yield 2.38 g of the pure product 10 (60% yield).

EXAMPLE 11

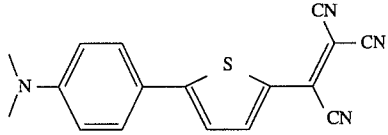

11

Tricyanovinyl derivative 11 was prepared by mixing the compound 4-(2-thienyl)dimethylaminobenzene (2.03 g, 10 mmol) with tetracyanoethylene (1.5 g, 12 mmol) in 20 mL dimethylformamide at 0° C. The 4-(2-thienyl) dimethylaminobenzene was prepared as described in *Tetrahedron Lett.*, 4743 (1990). The reaction mixture was stirred at room temperature for three hours and at 50° C. for another 20 hours. The reaction was then quenched with 100 mL water and the dark red colored aqueous solution was extracted with 500 mL methylene chloride. The organic layer was washed with water several times, dried over $Na_2SO_4$ and evaporated. The crude products were purified through a silica gel column eluted with a 1:1 ratio solution of methylene chloride and hexane to yield 2.43 g of the pure product 11 (80% yield).

EXAMPLE 12

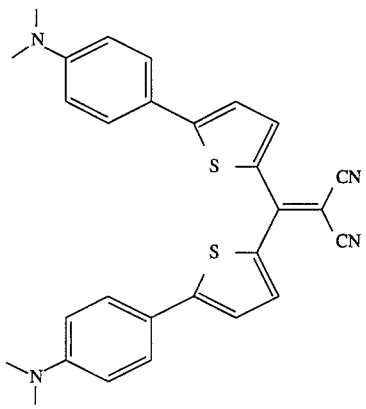

12

The dicyanovinyl derivative 12 was prepared by adding n-butyllithium (2.5 M, 3.8 mL, 9.5 mmol) to a stirred solution of 4-(2-thienyl) dimethylaminobenzene (1.82 g, 9 mmol) in 25 mL dry THF at −78° C. under an argon atmosphere. After stirring at −30° C. for two hours, the mixture was then added dropwise to a solution containing the tricyanovinyl compound 11 of Example 11 (2.74 g, 9 mmol) in 25 mL THF at −78° C. The resulting mixture was stirred for another four hours and the reaction was then quenched with 100 mL water. The THF was removed under reduced pressure and the aqueous solution was extracted with methylene chloride. The organic layer was separated, dried over $Na_2SO_4$ and evaporated. The crude products were purified through a silica gel column eluted with a 3:1 ratio solution of methylene chloride and hexane to yield 1.73 g of the pure product 12 (60% yield).

EXAMPLE 13 -Preparation Of 1-[4-(N-Pyrrolidino)Phenyl] -1-(2-Phenyl)-2,2-Dicyano Ethylene

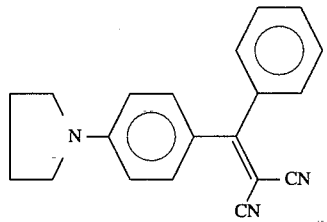

13

This dicyanovinyl compound of the present invention was prepared by slowly adding to a stirred solution of the compound 4 of Example 4 (2.48 g, 10 mmol) in 40 mL of dry THF at −78° C. under an argon atmosphere, a solution of phenyllithium in a 70:30 ratio solvent blend of cyclohexane and ether (1.8 M, 5.56 mL, 10 mmol). The phenyllithium was obtained from Aldrich. After 30 minutes, the mixture was warmed, washed with water and extracted with 200 mL dichloromethane. The organic layer was separated, dried over $Na_2SO_4$ and evaporated. The crude product was purified through a silica gel column eluted with a 1:1 ratio solution of dichloromethane and hexane to yield 2.40 g of the pure product 13 (80% yield).

19
EXAMPLE 14 -(Comparative Example)

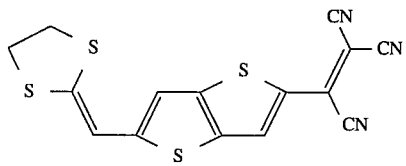

Preparation of a tricyanovinylated 1,3-dithiane substituted thienylthiophene 1Z was prepared by first adding n-butyllithium (2.5 M, 8.46 mL, 21.4 mmol) to a stirred solution of thienylthiophene (3.0 g, 21.4 mmol) in 60 mL THF at 0° C. The resulting mixture was maintained at 0° C. for 30 minutes. To this, tetramethyl ethylene diamine (3.2 mL, 21.4 mmol) was added and the solution was warmed to room temperature for one hour. The mixture was then recooled to 0° C., DMF (5.0 mL, excess) was added and the mixture was again allowed to warm to room temperature. After approximately one hour, the reaction was quenched with 10 mL water and stirred overnight. The THF was removed in vacuo and 100 mL of water was added. The product was extracted out of the aqueous layer using methylene chloride (2×200 mL). The combined extracts were dried ($Na_2SO_4$), concentrated and chromatographed (hexane: dichloromethane, 1:1) to yield an aldehyde (2.29 g, 64.0% yield) as a white solid.

The aldehyde (1.0 g, 6 mmol) was then added to a solution of 2-trimethylsilyl-1,3-dithiane (1.15 g, 6 mmol) and potassium t-butoxide (0.71 g, 6.3 mmol) in 50 mL THF at 0° C. After the addition, the mixture was stirred at room temperature under an argon atmosphere for two hours. The reaction mixture was quenched with 100 mL water, and the THF was removed under reduced pressure. The aqueous phase was extracted, dried and concentrated as above and the solvent concentration was followed by column chromatography (silica gel/hexane) to yield a 1,3-dithiane substituted thienyl thiophene (1.3 g, 80% yield).

The 1,3-dithiane substituted thienylthiophene was tricyanovinylated by mixing the 1,3-dithiane substituted thienylthiophene (1.0 g, 3.7 mmol) with tetracyanoethylene (0.5 g, 4 mmol) in 20 mL DMF at 0° C. The reaction mixture was stirred at room temperature for three hours and at 50° C. for another 20 hours. The reaction mixture was then quenched with 100 mL water, and the resulting dark blue colored aqueous solution was extracted with methylene chloride (4×250 mL). After washing the organic layer several times with water, the solvent was evaporated and dried as set forth above. The evaporation of the solvent followed by column chromatography, (silica gel, dichloromethane:hexane, 1:1) yielded a dark green tricyanovinylated 1,3-dithiane substituted thienylthiophene 14 (0.41 g, 30% yield).

EXAMPLE 15

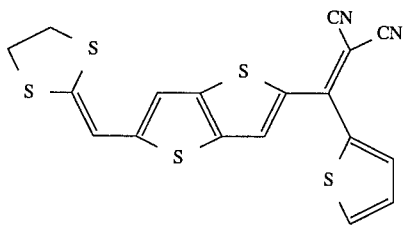

This dicyanovinyl compound of the present invention was prepared according to the method of Example 13, substituting a solution of the compound 14 of Example 14 (3.57 g,

20
10.0 mmol) for the compound 4 of Example 4 in 40 mL of THF. 3.0 g of the pure product 12 (75% yield) was obtained.

CHEMICAL AND THERMAL STABILITY STUDIES

The compounds of Examples 1, 5 and 8–12 were tested for their chemical and thermal stability, particularly with regard to the conditions commonly used in the preparation of aromatic polyimides. Compounds 8 and 11 served as controls. Thus, 10 mg of each of the above compounds was dissolved in a chloroform solution of a pre-imidized polyimide or an NMP solution of a polyamic acid. The resultant solutions were coated onto glass plates and heated under argon at 200° C., 240° C. and 280° C., respectively. The stability of each compound was determined by UV-visible spectroscopy. A decrease or change (spreading) of the absorption band was taken as an index of degradation. The results are summarized in Table I:

TABLE I

| | Stability of NLO Chromophores in a Preimidized Polyimide Host | | | Stability of NLO Chromophores in Curing Conditions of Polyamicacid | | |
|---|---|---|---|---|---|---|
| Compound | 200° C. | 240° C. | 280° C. | 200° C. | 240° C. | 280° C. |
| 4 | stable | sublime | — | stable | decomp. | — |
| 5 | stable | stable | stable | stable | stable | stable |
| 11 | stable | stable | stable | stable | decomp. | — |
| 12 | stable | stable | stable | stable | stable | stable |

The superior thermal and chemical stability of the NLO compounds of the present invention is evident. These compounds also possess the $\beta\mu$ values required of NLO materials, as summarized in Table II:

TABLE II

| Compound | $\lambda_{max}$ (nm) in dioxane | $\beta\mu$ ($10^{-48}$ esu) at $\lambda = 1.907$ μm |
|---|---|---|
| 10 | 419 | 320 |
| 9 | 536 | 480 |
| 5 | 478 | 470 |
| 12 | 545 | 1300 |

The NLO compounds of the present invention thus possess a combination of NLO properties and thermal and chemical stability heretofore unobtained by the prior art. At the same time, the compounds have good solubility, high laser damage thresholds, are easily synthesized and have well-known and understood chemical properties. The single-ring and fused-ring structures of the present invention containing five-membered heteroaromatic rings represent a versatile family of compounds that can be readily varied to increase their second order NLO properties.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A nonlinear optical compound of the formula:

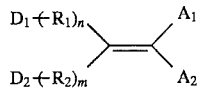

wherein $A_1$ and $A_2$ are independently selected from the group consisting of electron withdrawing moieties;

$R_1$ and $R_2$ are independently selected from the group consisting of aromatic rings, heteroaromatic rings and fused ring systems consisting of two or three aromatic or heteroaromatic rings, wherein at least one of $R_1$ or $R_2$ is a five-membered heteroaromatic ring or a fused ring system comprising a five-membered heteroaromatic ring;

n and m are independently integers from one to five, inclusive;

$D_1$ and $D_2$ are independently selected from the group consisting of hydrogen, electron donating groups and polymer attachment groups, with the proviso that at least one of $D_1$ and $D2$ is an electron donating group; and the compound formed by $A_1$, $A_2$, $D_1$, $D_2$, $R_1$ and $R_2$ possesses a delocalized resonance configuration.

2. The nonlinear optical compound of claim 1, wherein said five-membered heteroaromatic ring has the structure:

wherein Y is C or N and X is selected from the group consisting of O, S, Se, Te and N.

3. The nonlinear optical compound of claim 2, wherein both $R_1$ and $R_2$ are five-membered heteroaromatic rings or fused ring systems containing said five-membered heteroaromatic ring.

4. The nonlinear optical compound of claim 1, wherein $R_1$ and $R_2$ are independently selected from the group consisting of pyrrole, furan, thiophene, imidazole, oxazole, thiazole, triazole, tetrazole, pyrazole, pyrimidine, purine, quinolines, carbazole, benzene, naphthalene, furazan, pyrazine, indole, isoindole, indazole, phenothiazine, benzotriazole, anthracine, phenanthrene, quinazoline, pteridine and azophenanthrenes.

5. The nonlinear optical compound of claim 4, wherein $R_1$ and $R_2$ are independently selected from the group consisting of pyrrole, furan, thiophene, thiazole and oxazole.

6. The nonlinear optical compound of claim 1, wherein at least one of $R_1$ and $R_2$ is a fused ring system.

7. The nonlinear optical compound of claim 6, wherein both $R_1$ and $R_2$ are fused ring systems.

8. The nonlinear optical compound of claim 1, wherein $A_1$ and $A_2$ are independently selected from the group consisting of —$NO_2$, —CN, —CHO, —$COR_5$, —$COOR_5$, —$PO(OR_5)_2$, —$SO_2R_5$, —$SO_3R_5$ and —$PO(R_5)_2$, wherein $R_5$ is an alkyl group containing up to 15 carbon atoms, or $A_1$ and $A_2$ together comprise a ring moiety.

9. The nonlinear optical compound of claim 8, wherein $A_1$ and $A_2$ together comprise a ring moiety selected from the group consisting of N,N-dialkylbarbituric acids, N,N-dialkylthiobarbituric acids, rhodamines, hydrantoins, oxazolines and ring moieties having the structure:

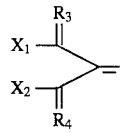

wherein $X_1$ and $X_2$ form a saturated or unsaturated five-to-eight-member cyclic ring or two-ring system having five-to eight-membered rings, and $R_3$ and $R_4$ are independently selected from the group consisting of O, S and —$CI_1I_2$, wherein $I_1$ and $I_2$ of $R_3$ and $R_4$ are independently selected from the group consisting of —CN, —$NO_2$, —$COR_5$, —$COOR_5$, —$SO_2R_5$, —$PO(R_5)_2$ and —$PO(OR5)_2$, and $R_5$ is an alkyl group containing up to 15 carbon atoms.

10. The nonlinear optical compound of claim 9, wherein $A_1$ and $A_2$ together comprise a moiety selected from the group consisting of 3-dicyanovinyl-indane-1-sulfone, 1,3-bissulfonylindane, indane-1,3-dione, 3-dicyanovinyl-indane-1-one and 1,3-bisdicyanovinyl indane.

11. The nonlinear optical compound of claim 8, wherein $A_1$ and $A_2$ comprise —$NO_2$ or —CN.

12. The nonlinear optical compound of claim 1, wherein $D_1$ and $D_2$ comprise electron donating groups independently selected from the group consisting of —$NR_6R_7$, —$OR_8$, —$SR_8$, —$TeR_8$, —$SeR_8$, —CH=$NR_9$, —CH=N—$NR_6R_7$ and —CH=C$[NR_6R_7]_2$, wherein $R_6$ and $R_7$ are independently selected from the group consisting of hydrogen, alkyl groups containing up to 12 carbon atoms and alkyl groups containing up to 12 carbon atoms having reactive functional groups selected from the group consisting of hydroxyl, ethylene, acetylene, amine, thiol, sulfonic acid and carboxylic acid, or $R_6$ and $R_7$ together form a cyclic group containing up to 8 carbon atoms; $R_8$ is selected from the group consisting of alkyl groups containing up to 6 carbon atoms; and $R_9$ is selected from the group consisting of hydrogen and alkyl groups containing up to 10 carbon atoms.

13. The nonlinear optical compound of claim 12, wherein $R_6$ and $R_7$ together form a cyclic group selected from the group consisting of pyrrolidine, piperidine, piperazine and morpholine groups.

14. The nonlinear optical compound of claim 1, wherein $D_1$ or $D_2$ comprise electron donating groups having the structure:

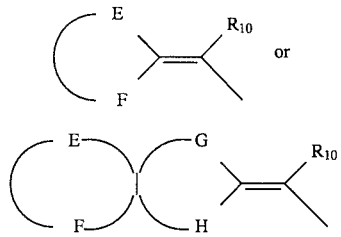

wherein E, F, G and H are members of a saturated or unsaturated five- to eight-membered cyclic ring or two-ring system having five- to eight-membered rings that are electron donating in nature and are independently selected from the group consisting of —CH—, —$CH_2$—, O, N, S, Se, Te and —NR—; and R and $R_{10}$ are independently selected from the group consisting of hydrogen, alkyl moieties containing up to 18 carbon atoms and functionalized alkyl moieties containing up to 18 carbon atoms, wherein said functionalized alkyl moieties are selected from the group consisting of alkoxy, aminoalkyl, alkylhalide, hydroxyalkyl, alkylsulfide, alkylthiol, alkylazide, alkylcarboxylic, alkylsulfonic, alkylalkene, alkylisocyanate, alkylisothiocyanate and alkylalkyne moieties.

15. The nonlinear optical compound of claim 14, wherein $D_1$ or $D_2$ comprise an electron donating group selected from the group consisting of 1,3-dithiolium, 2-benzo-1,3-dithiolium and 2-ethylenedithio-1,3-dithiolium moieties.

16. The nonlinear optical compound of claim 1, wherein said compound comprises up to two polymer attachment groups.

17. The nonlinear optical compound of claim 16, wherein said polymer attachment groups are selected from the group consisting of functionalized alkyl moieties containing between 3 and 12 carbon atoms, wherein said functionalized alkyl moieties are selected from the group consisting of alkoxy, aminoalkyl, alkylhalide, hydroxy alkyl, alkylsulfide, alkylthiol, alkylazide, alkylcarboxylic, alkylsulfonic, alkylalkene, alkylisocyanate, alkylisothiocyanate and alkylalkyne moieties.

18. The nonlinear optical compound of claim 16, wherein one of $D_1$ or $D_2$ comprises a first polymer attachment group.

19. The nonlinear optical compound of claim 18, wherein said nonlinear optical compound comprises a second polymer attachment group.

20. The nonlinear optical compound of claim 18, wherein said first polymer attachment group comprises an electron donating group having a polymer attachment group.

21. The nonlinear optical compound of claim 1, wherein n and m are, independently, one, two or three.

22. A combination exhibiting second order nonlinear optical properties comprising said nonlinear optical compound of claim 1 and a medium chemically inert to said nonlinear optical compound.

23. The combination of claim 22, wherein said nonlinear optical compound has an external field-induced molecular alignment.

24. The combination of claim 22, comprising a blend of said nonlinear optical compound in a chemically inert medium selected from the group consisting of polyacrylates, polymethacrylates, polyacrylamides, polycarbonates, polyamides, polyesters, polystyrenes, polyimides, polyether ketones, polyether ether ketones, polyphenylene ethers and copolymers thereof.

25. . The combination of claim 24, wherein said chemically inert medium comprises a polyimide.

26. The combination of claim 22, wherein said nonlinear optical compound comprises at least one polymer attachment group, and said polymer attachment groups are covalently linked to at least one polymer comprising one or more monomeric subunits having a reactive group capable of being covalently attached to a polymer attachment group, whereby said nonlinear optical compound is covalently linked to said polymers at said reactive groups of said subunits via said polymer attachment groups.

27. The combination of claim 26, wherein said polymer attachment groups are independently selected from the group consisting of functionalized alkyl moieties containing between 3 and 12 carbon atoms, wherein said functionalized alkyl moieties are selected from the group consisting of alkoxy, aminoalkyl, alkylhalide, hydroxyalkyl, alkylsulfide, alkylthiol, alkylazide, alkylcarboxylic, alkylsulfonic, alkylalkene, alkylisocyanate, alkylisothiocyanate and alkylalkyne moieties.

28. The combination of claim 26, wherein said polymers comprise a plurality of said monomeric subunits having reactive groups covalently substituted with a nonlinear optical compound via said polymer attachment groups, so that the ratio of said monomeric subunits having reactive groups covalently linked to a nonlinear optical compound to monomeric subunits without a nonlinear optical compound covalently linked thereto is between about 1:99 and about 50:50.

29. The combination of claim 28, wherein said ratio is between about 5:95 and about 40:60.

30. The combination of claim 29, wherein said ratio is about 25:75.

31. The combination of claim 28, wherein said monomeric subunits having reactive groups covalently substituted with a nonlinear optical compound via a polymer attachment group, and said monomeric subunits without a nonlinear optical compound covalently linked thereto are independently selected from the group consisting of acrylate, amide, acrylamide, styrene, vinyl halide, acrylonitrile, vinyl alcohol, vinyl acetate, monomeric subunits, and monomeric subunits of polyimides, polyesters, polyphenylene ethers, polyether ketones, polyether ether ketones, acid anhydrides, polyethylene, polypropylene, polyisobutylene, polyisoprene, polyurethanes, polyquinolines, epoxy polymers, polybenzoxazoles, polybenzothiazoles, polysulfones and polycarbonates.

32. The combination of claim 31, wherein said monomeric subunits having reactive groups covalently substituted with a nonlinear optical compound via a functionalized alkyl moiety comprise polyimide monomeric subunits.

33. The combination of claim 32, wherein said chemically inert medium comprises a polymer matrix within which said nonlinear optical compound is cured.

34. The combination of claim 33, wherein said polymer matrix comprises a polyimide.

35. The combination of claim 33, wherein said polymer matrix is crosslinked.

* * * * *

UNITED STATES PATENT AND TRADEMARK OFFICE
CERTIFICATE OF CORRECTION

PATENT NO. : 5,514,799
DATED : May 7, 1996
INVENTOR(S) : Varanasi et al.

It is certified that error appears in the above-identified patent and that said Letters Patent is hereby corrected as shown below:

Column 13, line 17, "hjigh" shuld read --high--.

Column 19, line 11, "IZ" should read --11--.

Column 21, line 22, "D2" should read --$D_2$--.

Column 22, line 14, "--PO(OR5)$_2$" should read -- --PO(OR$_5$)$_2$--.

Column 23, line 1, "moleties" should read --moieties--.

Signed and Sealed this

Twenty-third Day of July, 1996

Attest:

BRUCE LEHMAN

*Attesting Officer*     *Commissioner of Patents and Trademarks*